United States Patent [19]

Kinstler et al.

[11] Patent Number: 5,770,577
[45] Date of Patent: Jun. 23, 1998

[54] BDNF AND NT-3 POLYPEPTIDES SELECTIVELY LINKED TO POLYETHYLENE GLYCOL

[75] Inventors: Olaf Boris Kinstler; Qiao Yan, both of Thousand Oaks, Calif.

[73] Assignee: Amgen Inc., Thousand Oaks, Calif.

[21] Appl. No.: 340,131

[22] Filed: Nov. 14, 1994

[51] Int. Cl.$^6$ .................. A61K 38/00; A61K 39/385; C07K 16/00
[52] U.S. Cl. .............. 514/21; 514/12; 525/54.1; 530/391.9; 530/395; 530/409; 530/410; 530/839; 424/193.1; 424/194.1; 424/198.1
[58] Field of Search .................. 514/21, 12; 525/54.1; 530/391.9, 395, 409, 410, 839; 424/193.1, 194.1, 198.1

[56] References Cited

U.S. PATENT DOCUMENTS

| | | | |
|---|---|---|---|
| 4,002,531 | 1/1977 | Royer | 195/68 |
| 4,179,337 | 12/1979 | Davis et al. | 435/181 |
| 4,904,584 | 2/1990 | Shaw | 435/69.4 |
| 5,169,762 | 12/1992 | Gray et al. | 435/69.1 |
| 5,180,820 | 1/1993 | Barde et al. | 536/23.51 |
| 5,182,107 | 1/1993 | Friden | 424/85.91 |
| 5,229,500 | 7/1993 | Barde et al. | 530/399 |
| 5,252,714 | 10/1993 | Harris et al. | 530/391.9 |
| 5,260,308 | 11/1993 | Poduslo et al. | 514/21 |
| 5,264,209 | 11/1993 | Mikayama et al. | 424/85.2 |
| 5,389,529 | 2/1995 | Panayotatos et al. | 435/69.8 |
| 5,438,121 | 8/1995 | Barde et al. | 530/399 |
| 5,468,872 | 11/1995 | Glicksman et al. | 548/416 |

FOREIGN PATENT DOCUMENTS

| | | |
|---|---|---|
| 0 154 316 | 9/1985 | European Pat. Off. . |
| 0 335 423 | 10/1989 | European Pat. Off. . |
| 0 401 384 | 11/1989 | European Pat. Off. . |
| 0 473 268 | 3/1992 | European Pat. Off. . |
| 0473268 | 3/1992 | European Pat. Off. . |
| 0 539 167 | 4/1993 | European Pat. Off. . |
| WO 91/03569 | 3/1991 | WIPO . |
| WO 92/05254 | 4/1992 | WIPO . |

OTHER PUBLICATIONS

W.D. Snider, Cell, vol. 77, pp. 627–638 (1994).
Francis, *Focus on Growth Factors* 3(2):4–10 (1992).
Sada et al., *J. Ferment. Bioengin.* 71:137–139 (1991).
Abuchowski et al., *Enzymes as Drugs*, pp. 367–383 (1981).
Delgado et al., *Sep. Using Aq. Phase Sys.*, pp. 211–213 (1989).
Chamow et al., *Bioconjug. Chem.* 5:133–140 (1994).
Barde et al., *Neuron* 2:1525–1534 (1989).
Snider et al., *Cell* 77:627–638 (1994).
Yan et al., *J. Neurosci.* 14(9):5281–5291 (1994).
Yan et al., *Soc. Neurosci. Abs.* 20:1306 (1994).
Yan et al., *Nature* 360:753–755 (1992).
Oppenheim et al., *Nature* 360:755–757 (1992).
Sendtner et al., *Nature* 360:757–759 (1992).
Yan et al., *J. Neurosci.*, 8(9):3481–3498 (1988).
Lindsay et al., *Dev. Biol.* 112:319–328 (1984).
Lams et al., *Brain Res.* 475:401–406 (1988).
Armstrong et al., *J. Comp. Neurol.*, 304:596–607 (1991).
Ferguson et al., *J. Comp. Neurol.*, 313:680–692 (1991).

*Primary Examiner*—Cecilia J. Tsang
*Assistant Examiner*—Abdel A. Mohamed
*Attorney, Agent, or Firm*—Richard J. Mazza; Ron Levy; Steven M. Odre

[57] ABSTRACT

Derivatives of the neurotrophic factors BDNF and NT-3 have been prepared by attachment of these polypeptides to a water soluble polymer, for instance, polyethylene glycol.

16 Claims, 8 Drawing Sheets

$$\downarrow \text{NaCNBH}_3$$

FIG.3

Synthesis of mono-MePEG-BDNF(NT-3) conjugates.

BDNF AND NT-3 POLYPEPTIDES SELECTIVELY LINKED TO POLYETHYLENE GLYCOL

FIELD OF THE INVENTION

The present invention relates to a novel class of BDNF and NT-3 derivatives wherein a BDNF or NT-3 molecule is attached to a water soluble polymer, and to a method for preparing such derivatives.

BACKGROUND OF THE INVENTION

Proteins for therapeutic use are currently available in suitable forms in adequate quantities largely as a result of the advances in recombinant DNA technologies. Chemical derivatives of such proteins may effectively block a proteolytic enzyme from physical contact with the protein backbone itself, and thus prevent degradation. Additional advantages may include, under certain circumstances, increasing the stability and circulation time of the therapeutic protein and decreasing immunogenicity. However, it should be noted that the effect of modification of a particular protein cannot be predicted. A review article describing protein modification and fusion proteins is Francis, *Focus on Growth Factors* 3:4–10, published by Mediscript, Mountview Court, Friern Barnet Lane, London, England (1992).

Polyethylene glycol ("PEG" or "peg") is one such chemical moiety which has been used in the preparation ("pegylation") of therapeutic protein products ("pegylated proteins"). For example, pegylated adenosine deaminase is approved for treating severe combined immunodeficiency disease; pegylated superoxide dismutase has been used in clinical trials for treating head injury; pegylated alpha interferon has teen tested in phase I clinical trials for treating hepatitis; pegylated glucocerebrosidase and pegylated hemoglobin are reported to have been in preclinical testing. For some proteins, the attachment of polyethylene glycol has been shown to protect against proteolysis, Sada et al., *J. Fermentation Bioengineering* 71:137–139 (1991). Methods for the attachment of certain polyethylene glycol moieties are available. See U.S. Pat. No. 4,179,337 (Davis et al.), and U.S. Pat. No. 4,002,531 (Royer). For a review, see Abuchowski et al., in Other water soluble polymers have been used to modify proteins, such as copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymers, and polyamino acids (either homopolymers or random copolymers).

For polyethylene glycol, a variety of means have been used to attach the polyethylene glycol molecules to the protein. Generally, polyethylene glycol molecules are connected to the protein via a reactive group found on the protein. Amino groups, such as those on lysine residues or at the N-terminus, are convenient for such attachment. For example, the Royer patent, above, states that reductive alkylation was used for attachment of polyethylene glycol molecules to an enzyme. European patent application 0 539 167, published Apr. 28, 1993, states that peptides and organic compounds with free amino group(s) are modified with an imidate derivative of PEG or related water-soluble organic polymers. U.S. Pat. No. 4,904,584 (Shaw) relates to the modification of lysine residues in proteins for the attachment of polyethylene glycol molecules via reactive amine groups.

One specific therapeutic protein which has been chemically modified is granulocyte colony stimulating factor, i.e., G-CSF. See European patent publications EP 0 401 384, EP 0 473 268, and EP 0 335 423. Another example is pegylated IL-6, described in U.S. Pat. No. 5,264,209 (Mikayama et al.). Also, European patent application 0 154 316, published Sep. 11, 1985, reports reacting a lymphokine with an aldehyde of polyethylene glycol.

Pegylation of protein molecules will generally result in a mixture of chemically modified protein molecules. As an illustration, protein molecules with five lysine residues and a free amino group at the N-terminus reacted in the above methods may result in a heterogeneous mixture, some having six polyethylene glycol moieties, some five, some four, some three, some two, some one, and some zero. Among the molecules with several, the polyethylene glycol moieties may not be attached at the same location on different molecules. The above methods typically require a linking moiety between the protein and the polyethylene glycol molecule. The procedure described by Delgado et al. in "Coupling of PEG to Protein by Activation with Tresyl Chloride, Applications In Immunoaffinity Cell Partitioning", *Separations Using Aqueous Phase Systems, Applications In Cell Biology and Biotechnology,* Plenum Press, New York, N.Y. (1989), at pages 211–213, involves the use of tresyl chloride and results in no linking group between the polyethylene glycol and protein moieties. This method may be difficult to use to produce therapeutic products because the use of tresyl chloride may result in toxic by-products.

Chamow et al., *Bioconjugate Chem.* 5:133–140 (1994) report the modification of CD4 immunoadhesin with monomethoxypolyethylene glycol ("MePEG glycol") aldehyde via reductive alkylation. The authors report that the in vitro binding capability of the modified CD4-IgG (to the protein gp 120) decreased at a rate correlated to the extent of MePEGylation.

Brain derived growth factor (BDNF) and neurotrophin-3 (NT-3) are known polypeptides belonging to a distinct class of neurotrophic factors called neurotrophins that includes nerve growth factor (NGF). These factors promote the survival and maintenance of functions of neurons and are prime candidates for the therapeutic treatment of neurodegenerative diseases. Barde et al., *Neuron* 2:1525–1534 (1989); Snider et al., *Cell* 77:627–638 (1994). Methods for the identification and recombinant production of these factors have been described in the patent literature; see U.S. Pat. No. 5,169,762 (Gray et at.) for NGF, U.S. Pat. Nos. 5,180,820 (Barde et al.) and 5,229,500 (Barde et al.) for BDNF, and published PCT Application No. WO 91/03569 for NT-3.

SUMMARY OF THE INVENTION

Briefly stated, in one aspect, the present invention provides BDNF and NT-3 derivatives in which the BDNF or NT-3 polypeptide moiety is attached to a water soluble polymer.

More particularly, the present invention includes BDNF and NT-3 derivatives wherein the polypeptides are reacted with reactive (i.e., "activated") water soluble polymer moieties so as to attach the polymer to the polypeptide. Such attachment may be accomplished by reactions discussed herein, such as acylation or alkylation. Acylation or alkylation with polyethylene glycol or other water soluble polymer may be carried out under conditions whereby the major product is mono- or poly-derivatized. Polyderivatization generally involves attachment of polyethylene glycol or other water soluble polymer to the ε-amino groups of lysine residues of the polypeptide and may additionally involve attachment of the polymer to the N-terminus of the polypeptide. Monoderivatization preferably involves attachment of the polymer to the α-amino group of the N-terminal residue of a BDNF or NT-3 polypeptide moiety, thereby providing for selective attachment of a water soluble polymer moiety onto the N-terminus of the polypeptide. This provides for a substantially homogeneous preparation of polymer/BDNF or polymer/NT-3 conjugate molecules as well as (if polyethylene glycol is used) a preparation of pegylated BDNF or NT-3 molecules having the polyethylene glycol moiety directly coupled to the BDNF or NT-3 moiety.

The BDNF and NT-3 derivatives of this invention are useful for the same purposes for which trophic factors BDNF and NT-3 are known to be useful, in particular, for promoting the survival and maintenance of neurons in vitro and in vivo, and as potential therapeutic agents for the treatment in humans of neurodegenerative diseases, such as Parkinson's, amyotrophic lateral sclerosis (ALS), Huntington's disease, retinal degeneration, peripheral neuropathies, and Alzheimer's disease, among others. As shown in some of the examples further below, derivatization in accordance with this invention can also result in an enhanced ability of the molecule to migrate through brain tissue, thus resulting in greater ease of delivery to therapeutic targets located within the brain.

In another aspect, also described in further detail below, this invention provides a method for the preparation of BDNF and NT-3 derivatives of the above mentioned variety in which water soluble polymers, especially polyethylene glycol, are attached to the α-amino group at the N-terminus of the polypeptide (BDNF or NT-3), to obtain a homogeneous population of derivatized molecules, i.e., conjugates of these polypeptides with the polymer.

BRIEF DESCRIPTION OF THE FIGURES

FIG. 4 shows the choline acetyltransferase (ChAT) immunohistochemistry of axotomized facial motoneurons in an in vivo animal model for loss of peripheral nerve function. Yan et al., *J. Neurosci.* 14(9):5281–5291 (1994). The right facial nerves of adult female rats were transected and the animals were treated subcutaneously each day for seven days as follows: PBS (FIG. 4A), unpegylated BDNF at 5 milligrams per kilogram of body weight, mg/kg (FIG. 4B), N-terminally pegylated BDNF at 0.3 mg/kg (FIG. 4C), or randomly pegylated BDNF at 0.3 mg/kg (FIG. 4D). In the PBS-treated rats, axotomy resulted in a large drop in ChAT immunoreactivity in the lesioned facial nucleus (FIG. 4A facial nucleus on right hand side). In contrast, treatment with both unpegylated BDNF and pegylated BDNF (FIGS. 4B, 4C and 4D) attenuated the lesion-induced drop of ChAT immunoreactivity. Symbols are as follows: FN, facial nucleus; py, pyrimidal tract; Sp5, nucleus of spinal tract of trigeminal. Scale bar (in panel D) represents 1 mm.

FIG. 8 shows the retrograde transport through brain tissue of unpegylated BDNF (FIG. 8A and FIG. 8B) and pegylated BDNF (FIG. 8C and FIG. 8D) to interiorly located dopaminergic neurons after infusion into the striatum of the brain in live rats, using the same procedure described in FIG. 7. FIG. 8B and FIG. 8D are enlargements of the squared sections in FIG. 8A and FIG. 8C, respectively. Symbols in FIG. 8A have the following meaning: SNC, substantia nigra compacta; SNR, substantia nigra reticulata; and VTA, ventral tegmental area. The bar in FIG. 8D indicates 500 μm for FIG. 8A and FIG. 8C, and 200 μm for FIG. 8B and FIG. 8D.

DETAILED DESCRIPTION OF THE INVENTION

Contemplated for use in the practice of this invention are BDNF and NT-3 of native (i.e., naturally occurring) sequence, as well as fragments, precursors and polypeptide molecules representing one or more amino acid substitutions, deletions or additions derived from the native sequence which exhibit biological properties similar to molecules of the native sequence, e.g., chimeras, analogs, and the like. Consequently, unless specifically indicated otherwise, the terms "BDNF" and "NT-3" shall be taken herein to mean these polypeptides in any of the foregoing forms.

Methods are known for the preparation of BDNF and NT-3, particularly by recombinant means, which is typically the most practical for obtaining large quantities. Useful procedures are described in the scientific and patent literature, including those set forth in the above mentioned U.S. Pat. Nos. 5,180,820 and 5,229,500, and in published PCT application WO 91/03569, all of which are incorporated herein by reference. Particularly preferred for use in the practice of this invention are BDNF and NT-3 of native sequence as expressed recombinantly in prokaryotic and eukaryotic cells, including recombinant polypeptide products expressed from the human nucleotide sequences ("r-HuBDNF" and "r-HuNT-3"), including those expressed in bacterial cells to include a methionine residue at the N-terminus (i.e., "r-metBDNF" and "r-metNT-3"). Examples of such polypeptides are those having the sequences shown in SEQ ID No: 1 ("r-HuBDNF"), SEQ ID NO: 2 ("r-metHuBDNF"), SEQ ID NO: 3 ("r-HuNT-3") and SEQ ID NO: 4 ("r-metHuNT-3").

Pegylation of BDNF and NT-3 may be carried out by any of the pegylation reactions known in the art. See, for example: *Focus on Growth Factors* 3(2):4–10 (1992); EP 0 154 316; EP 0 401 384; and the other publications cited herein that relate to pegylation. Preferably, the pegylation is carried out via an acylation reaction or an alkylation reaction with a reactive polyethylene glycol molecule (or an analogous reactive water-soluble polymer). These preferred means for derivatization with polyethylene glycol are discussed below in greater detail.

Acylation

Figure 6:
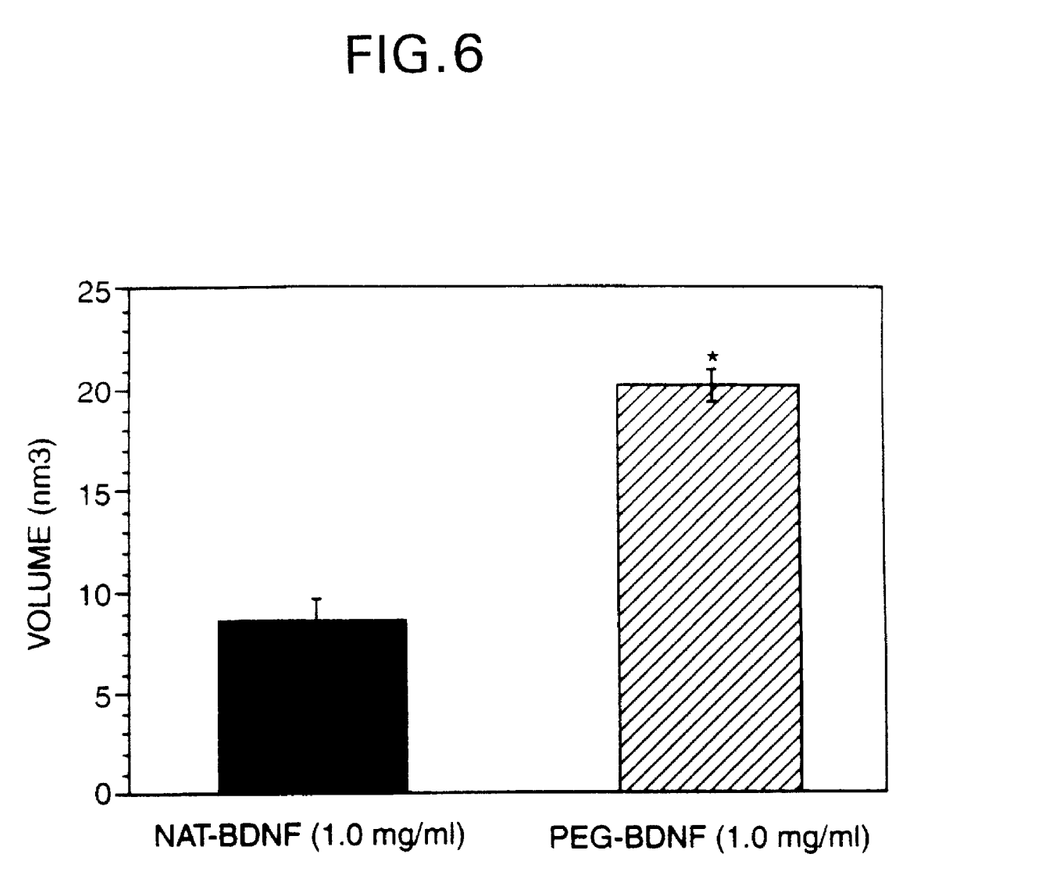
FIG. 6 is a bar graph showing the penetration of unpegylated BDNF ("NAT-BDNF") or pegylated BDNF ("PEG-BDNF") into the brain of live rats after single injection into the center of the right striatum. Twenty hours later, the animals were perfuse-fixed with 4% para formaldehyde. The brains were removed, sectioned, and stained with a specific antibody to BDNF using the procedure described by Yan et al. in *Soc. Neurosci. Abs.* 20:1306 (1994). The total volume of BDNF penetration into the brain tissue was quantified by integration of all BDNF immunoreactive tissue sections. Values are stated as mean ± SEM (n=4). The data were analyzed by the Student t test. *, $p<0.0001$.

Pegylation by acylation generally involves reacting an active ester derivative of polyethylene glycol (PEG) with a BDNF or NT-3 polypeptide. Virtually any reactive PEG molecule may be used to carry out the pegylation of these polypeptides. A preferred activated PEG ester is PEG esterified to N-hydroxysuccinimide ("NHS"). As used herein, "acylation" is contemplated to included without limitation the following types of linkages between BDNF or NT-3 and a water soluble polymer such as PEG: amide, carbamate, urethane, and the like; See *Bioconjugate Chem.* 5:133–140 (1994). Reaction conditions may be selected from any of those known in the art or those subsequently developed, but should avoid conditions such as temperature, solvent and pH that would inactivate the BDNF or NT-3 species to be modified. Reaction conditions that apply generally will be described below. An exemplary reaction with an NHS ester of monomethoxy-PEG is depicted in FIG. 6.

Pegylation by acylation will generally result in a polypegylated BDNF or NT-3 product, wherein the lysine ε-amino groups are pegylated via an acyl linking group. Preferably, the connecting linkage will be an amide. Also preferably, the resulting product will be substantially (e.g., $\geq 95\%$) mono, di- or tri-pegylated. However, some species with higher degrees of pegylation (up to the maximum number of lysine ε-amino acid groups of BDNF and NT-3 plus one α-amino group at the amino terminus of BDNF or NT-3) will normally be formed in amounts depending on the specific reaction conditions used. If desired, more purified pegylated species may be separated from the mixture containing unreacted species by standard purification techniques, including, among others, dialysis, salting-out, ultrafiltration, ion-exchange chromatography, gel filtration chromatography and electrophoresis.

Alkylation

Figure 7:
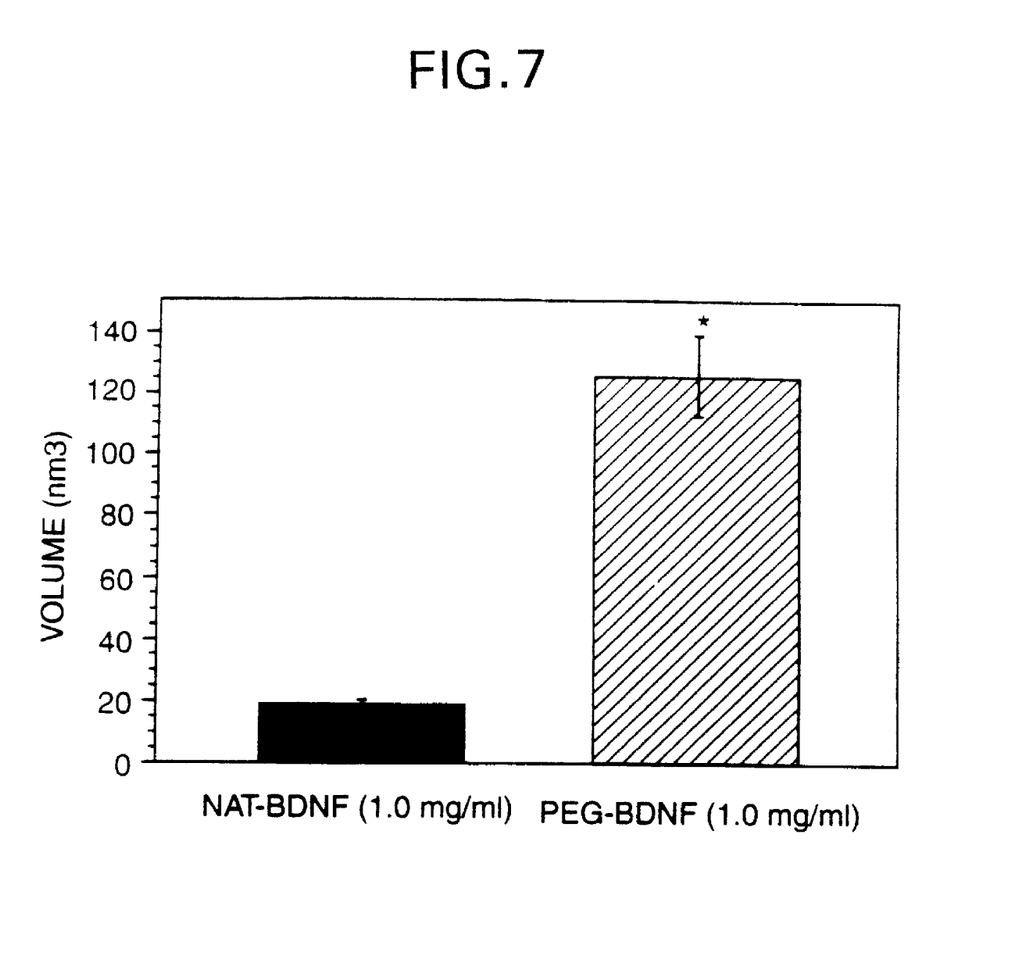
FIG. 7 is a bar graph showing the penetration of unpegylated BDNF and pegylated BDNF into the brain of live rats after continuous local administration over a period of seven days. The total volume of BDNF penetration was quantified the same as in FIG. 6. Values are stated as mean ± SEM (n=4). The data were analyzed by the Student t-test. *, $p<0.0001$.

Pegylation by alkylation generally involves reacting an aldehyde derivative of PEG with a polypeptide such as BDNF or NT-3 in the presence of a reducing agent. Pegylation by alkylation can also result in polypegylated BDNF or NT-3. An exemplary reductive alkylation reaction to yield a polypegylated product is shown in FIG. 7. In addition, one can manipulate the reaction conditions as described herein to favor pegylation substantially only at the α-amino group of the N-terminus of the BDNF or NT-3 polypeptide (i.e., a monopegylated species). An exemplary reductive alkylation reaction with BDNF or NT-3 to yield a monopegylated product is shown in FIG. 8. In either case of monopegylation or polypegylation, the PEG groups are preferably attached to the polypeptide via a —$CH_2$—NH— group. With particular reference to the —$CH_2$— group, this type of linkage is referred to herein as an "alkyl" linkage.

Derivatization via reductive alkylation to produce a monopegylated product exploits the differential reactivity of different types of primary amino groups (lysine versus the N-terminal) available for derivatization in BDNF or NT-3. The reaction is performed at a pH (see below) which allows one to take advantage of the $pK_a$ differences between the ε-amino groups of the lysine residues and that of the α-amino group of the N-terminal residue of the polypeptide. By such selective derivatization, attachment of a water soluble polymer that contains a reactive group, such as an aldehyde, to a polypeptide is controlled. The conjugation with the polymer takes place predominantly at the N-terminus of the polypeptide and no significant modification of other reactive groups, such as the lysine side chain amino groups, occurs. In one important aspect, the present invention provides for a substantially homogeneous preparation of monopolymer/BDNF or monopolymer/NT-3 conjugate molecules, meaning BDNF or NT-3 to which a polymer molecule has been attached substantially (i.e., $\geq 90\%$) in a single location only. More specifically, if polyethylene glycol is used, the present invention also provides for pegylated BDNF or NT-3 lacking possibly antigenic linking groups and having the polyethylene glycol molecule directly coupled to the BDNF or NT-3 polypeptide.

Thus, in a preferred aspect, the present invention relates to pegylated BDNF and NT-3 wherein the PEG group(s) is (are) attached via acyl or alkyl linkages. As discussed above, such products may be monopegylated or polypegylated (e.g., containing 2–6, preferably 2–5, PEG groups). The PEG groups are generally attached to the polypeptide at the α and/or ε amino of the polypeptide chain, but it is also contemplated that the PEG groups could be attached to any amino group of the polypeptide structure which is sufficiently reactive to become attached to a PEG group under suitable reaction conditions.

The polymer molecules used in both the acylation and alkylation approaches may be selected from among water soluble polymers or a mixture thereof. The polymer selected should be water soluble so that the polypeptide to which it is attached does not precipitate in an aqueous environment, such as a physiological environment. The polymer selected should be modified to have a single reactive group, such as an active ester for acylation or an aldehyde for alkylation, preferably, so that the degree of polymerization may be controlled as provided for in the present method. A preferred reactive PEG aldehyde is polyethylene glycol propionaldehyde, which is water stables or mono C1–C10 alkoxy or aryloxy derivatives thereof (see U.S. Pat. No. 5,252,714). The polymer may be branched or unbranched. Preferably, for therapeutic use of the end-product preparation, the polymer will be pharmaceutically acceptable. The water soluble polymer may be selected from the group consisting of, for example, polyethylene glycol (e.g., monomethoxy-polyethylene glycol), dextran, poly-(N-vinyl pyrrolidone), propylene glycol homopolymers, polypropylene oxide/ethylene oxide copolymers, polyoxyethylated polyols (e.g., glycerol) and polyvinyl alcohols. For the acylation reactions, the polymer selected should have a single reactive ester group. For the present reductive alkylation, the polymer selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

A particularly preferred water-soluble polymer for use herein is polyethylene glycol. As used herein, polyethylene glycol is meant to encompass any of the forms of PEG that have been used to derivatize other proteins, such as mono-(C1–C10) alkoxy- or aryloxy-polyethylene glycol.

In general, the derivatization may be performed under any suitable condition used to react a biologically active substance with an activated water soluble polymer molecule. Methods for preparing pegylated BDNF or NT-3 will generally comprise the steps of (a) reacting a BDNF or NT-3 polypeptide with polyethylene glycol (such as a reactive ester or aldehyde derivative of PEG) under conditions whereby BDNF or NT-3 becomes attached to one or more PEG groups, and (b) obtaining the reaction product. In general, the optimal reaction conditions for the acylation reactions will be determined case-by-case based on known parameters and the desired result. For example, the larger the ratio of PEG: protein, the greater the percentage of polypegylated product.

In the method of this invention, reductive alkylation to produce a substantially homogeneous population of monopolymer/polypeptide conjugate molecule will generally comprise the steps of: (a) reacting a BDNF or NT-3 polypeptide with a reactive PEG molecule under reductive alkylation conditions, at a pH suitable to permit selective modification of the α-amino group at the amino terminus of the polypeptide, and (b) obtaining the reaction product.

For a substantially homogeneous population of monopolymer/BDNF or monopolymer/NT-3 conjugate molecules, the reductive alkylation reaction conditions are those which permit the selective attachment of the water soluble polymer moiety to the N-terminus of the polypeptide. Such reaction conditions generally provide for $pK_a$ differences between the lysine ε-amino groups and the α-amino group at the N-terminus (the pKa being the pH at which 50% of the amino groups are protonated and 50% are not). The pH also affects the ratio of polymer to polypeptide to be used. In general, if the pH is lower, a larger excess of polymer to polypeptide will be desired (i.e., the less reactive the N-terminal α-amino group, the more polymer needed to achieve optimal conditions). If the pH is higher, the polymer:polypeptide ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer number of polymer molecules which may be attached to the polypeptide. Similarly, branching of the polymer should be taken into account when optimizing these parameters. Generally, the higher the molecular weight (or the more branches) the higher the polymer:polypeptide ratio. In general, for the pegylation reactions contemplated herein, the preferred average molecular weight for the polymer is from about 2 kDa to about 100 kDa (the term "about" indicating ±1 kDa). A more preferred average molecular weight is from about 5 kDa to about 50 kDa, and especially from about 12 kDa to about 25 kDa. The ratio of water-soluble polymer to BDNF or NT-3 will generally range from 1:1 to 100:1, preferably (for polypegylation) 1:1 to 20:1 and (for monopegylation) 1:1 to 5:1.

Using the conditions indicated above, reductive alkylation in accordance with this invention will provide for selective attachment of the polymer to any BDNF or NT-3 polypeptide protein having an α-amino group at the amino terminus, and provide for a substantially homogenous preparation of monopolymer/polypeptide protein conjugate. The term "monopolymer/polypeptide conjugate" is used here to mean a composition comprised of a single polymer molecule attached to a BDNF or NT-3 molecule. The monopolymer/polypeptide conjugate will have a polymer molecule located at the N-terminus, but not on lysine side groups. The preparation will preferably be greater than 80% monopolymer/polypeptide conjugate, and more preferably greater than 90% monopolymer/polypeptide conjugate, with the remainder of observable molecules being unreacted (i.e., polypeptide lacking the polymer moiety). The examples below provide for a preparation which is at least about 90% monopolymer/polypeptide conjugate, and about 10% unreacted polypeptide. The monopolymer/polypeptide conjugate is biologically active.

For the present reductive alkylation, the reducing agent should be stable in aqueous solution and preferably be able to reduce only the Schiff base formed in the initial process of reductive alkylation. Preferred reducing agents may be selected from the group consisting of sodium borohydride, sodium cyanoborohydride, dimethylamine borane, timethylamine borane and pyridine borane. A particularly preferred reducing agent is sodium cyanoborohydride.

Other reaction parameters, such as solvent, reaction times, temperatures, etc., as well as the means of purification of products, can be determined case-by-case based on the published information relating to derivatization of proteins with water soluble polymers (see the publications cited herein). Exemplary details are shown in the Examples given below.

One may choose to prepare a mixture of polymer/polypeptide conjugate molecules by acylation and/or alkylation methods, and the advantage provided herein is that one may select the proportion of monopolymer/polypeptide conjugate to include in the mixture. Thus, if desired, one may prepare a mixture of various polypeptide with various numbers of polymer molecules attached (i.e., di-, tri-, tetra-, etc.) and combine with the monopolymer/polypeptide conjugate material prepared using the present methods, and thus have a mixture with a predetermined proportion of monopolymer/polypeptide conjugate.

As mentioned, polymer/polypeptide conjugates in accordance with this invention can be used for the same purposes for which BDNF and NT-3 are known to be useful. These polypeptides have been previously shown to be effective, for instance, as trophic factors that promote the survival and maintenance of neurons in vitro, thus enabling the study and use of neurons in research. Such cells are normally very difficult to keep alive in culture. These same biological activities support the use of such factors in vivo for the neurological study of animals and offer the potential as therapeutic agents for the treatment of neurodegenerative diseases which are associated with losses in neuron function.

For therapeutic purposes, polymer/polypeptide conjugates of this invention may be formulated into and administered in any sterile biocompatible pharmaceutical carrier, including but not limited to saline, buffered saline, dextrose and water. The amount of the BDNF/polymer or NT-3/polymer conjugate that will be effective in the treatment of a particular disorder or condition will depend on the nature of the disorder or condition and can be determined by standard clinical techniques. Where possible, it is desirable to determine the dose-response curve for the pharmaceutical compositions of the invention first in vitro, for example, as in the BDNF and NT-3 bioassay systems described in the literature, and then in useful animal models prior to testing in humans. Methods of administration will include intradermal, intramuscular, intraperitoneal, intravenous, subcutaneous, intranasal, pulmonary and oral. In addition, it may be desirable to introduce the pharmaceutical compositions into the central nervous system by any suitable route, including intraventricular or intrathecal injection. Further, it may be desirable to administer the pharmaceutical compositions locally to the area in need of treatment. This may be achieved, for example, by local infusion during surgery, by injection, by means of a catheter, or by use of an implant of a porous, non-porous, gelatinous, fibrous or membranous material.

DESCRIPTION OF SPECIFIC EMBODIMENTS

The preparation of particular BDNF and NT-3 derivatives in accordance with this invention and their physical and biological properties are shown in the following text. These examples are presented to more fully illustrate the present invention and are not intended to be limiting. In these examples, human BDNF and NT-3 as prepared recombinantly in *E. coli* (i.e., r-metHuBDNF and r-metHuNT-3) were used, unless otherwise specified.

EXAMPLE 1

Preparation of monoMPEG(6 kDa)-BDNF conjugate with site of attachment at the N-terminal α-amino group(s)

To a cooled (4° C.), stirred solution of r-metHuBDNF (2.5 mg/ml) in 100 mM sodium phosphate, pH 4.0, containing 20 mM NaCNBH$_3$, there was added a two-fold molar excess of activated methoxypolyethylene glycol (MPEG) aldehyde, having an average molecular weight of 6,000 daltons (i.e., 6 kDa).

The extent of protein modification during the course of the reaction was monitored by size exclusion chromatography using a Superose 6HR 10/30 column (Pharmacia) eluted at a flow rate of 0.4 ml/min with 100 mM sodium phosphate, pH 6.9, containing 0.5M NaCl. After ten hours, analysis by size exclusion chromatography indicated that all of the polypeptide (which in solution exists as a dimer) had been essentially converted to the two possible forms of the N-terminally pegylated derivative: MPEG conjugated to one, or to both, of the N-termini of the BDNF dimer.

The reaction mixture was then diluted a total of five times with sterile water and applied to a HiLoad 16/10 S Sepharose HP ion exchange column (Pharmacia) equilibrated with 20 mM sodium phosphate buffer, pH 7.5. The reaction mixture was loaded onto the column at a flow rate of 1 ml/min, and the unreacted MPEG aldehyde eluted with three column volumes of the same buffer. A linear five hundred-minute gradient from 0% to 100% of 20 mM sodium phosphate, pH 7.5, containing 0.75M NaCl, was used to elute the two forms of the N-terminally pegylated BDNF dimer. Fractions containing the MPEG-BDNF derivatives were pooled, concentrated, and filtered sterile.

EXAMPLE 2

Preparation of monoMPEG(20 kDa)-BDNF conjugate with site of attachment at the N-terminal α-amino group(s)

The procedure of Example 1 was repeated, except using a methoxypolyethylene glycol (MPEG) aldehyde of 20,000 daltons (20 kDa) and a pH of 5.0.

EXAMPLE 3

Preparation of polyMPEG(6 kda)-BDNF conjugates by reductive alkylation with MPEG aldehydes To cooled (4° C.), stirred solution of r-metHuBDNF (10 mg/ml) in 100 mM BICINE, pH 8, containing 20 mM NaCNBH$_3$, was added a four-fold molar excess of methoxypolyethylene glycol (MPEG) activated aldehyde, having an average molecular weight of 6 kDa.

The extent of protein modification during the course of the reaction was monitored by size exclusion chromatography using a Superose 6HR 10/30 column (Pharmacia) eluted at 0.4 ml/min with 100 mM sodium phosphate, pH 6.9, containing 0.5M NaCl. After ten hours, analysis by size exclusion chromatography indicated that all of the polypeptide had been modified with MPEG.

The reaction mixture was then diluted five-fold with sterile water, the pH was adjusted to 7 (using phosphoric acid), and the mixture was applied to a HiLoad 16/10 S Sepharose HP ion exchange column (Pharmacia) equilibrated with 20 mM sodium phosphate buffer, pH 7.5. The reaction mixture was loaded on the column at a flow rate of 1 ml/min and unreacted MPEG aldehyde eluted with three column volumes of the same buffer. A linear five hundred-minute gradient from 0% to 100% of 20 mM sodium phosphate, pH 7.5, containing 0.75M NaCl, was used to elute the MPEG-BDNF conjugates. Fractions containing the MPEG-BDNF conjugates were pooled, concentrated, and sterile filtered.

EXAMPLE 4

Preparation of polyMPEG(6 kDa)-BDNF conjugates by reductive acylation with MPEG aldehydes The procedure of Example 3 was repeated, except that a six-fold molar excess of MPEG aldehyde was used.

EXAMPLE 5

Preparation of polyMPEG(6 kDa)-BDNF conjugates by acylation with activated MPEG derivatives To a cooled (4° C.), stirred solution of r-metHuBDNF (6 mg/ml) in 0.1M BICINE buffer, pH 8, there were added to a four-fold molar excess of succinimidyl esther of carboxymethyl MPEG, having an average molecular weight of 6 kDa. The polymer was dissolved by gentle stirring and the reaction was continued at the same temperature.

The extent of protein modification during the course of the reaction was monitored by size exclusion chromatography using a Superose 6HR 10/30 column (Pharmacia) eluted at 0.4 ml/min with 100 mM sodium phosphate, pH 6.9, containing 0.5M NaCl. After three hours, the size exclusion chromatography indicated that all of the BDNF dimer had been modified with MPEG.

The reaction mixture was then diluted four-fold with sterile water and the pH of the mixture adjusted to 7 (using 0.5M phosphoric acid). This solution was applied to HiLoad 16/10 S Sepharose HP ion exchange column (Pharmacia) equilibrated with 20 mM sodium phosphate buffer, pH 7.5. The unreacted MPEG aldehyde was eluted with three column volumes of the same buffer. A linear five hundred-minute gradient from 0% to 100% of 20 mM sodium phosphate, pH 7.5, containing 0.75M NaCl, was used to elute the MPEG-BDNF conjugates. Fractions containing MPEG-BDNF conjugates were pooled, concentrated, and sterile filtered.

EXAMPLE 6

Preparation of polyMPEG(6 kdDa)-BDNF conjugates by acylation with activated MPEG derivatives The procedure of Example 5 was repeated, except using an equal mole-to-mole ratio of reactants.

EXAMPLE 7
Preparation of polyMPEG(20 kdDa)-BDNF conjugates by acylation with activated MPEG derivatives The procedure of Example 5 was repeated, except using an MPEG succinimidyl propionate having an average molecular weight of 20 kDa, and six-fold molar excess of MPEG to BDNF dimer.

EXAMPLE 8
Preparation of monoMPEG (20 kDa)-NT-3 conjugate with site of attachment at the N-terminal α-amino residue To a cooled (4° C.), stirred solution of r-metHuNT-3 (4.77 mg/ml) in 20 mM sodium acetate, pH 4.0, containing 150 mM NaCl and 20 mM NaCNBH$_3$, there was added a three-fold molar excess of activated MPEG, having an average molecular weight of 20 kDa.

The extent of protein modification during the course of the reaction was monitored by size exclusion chromatography using a Superose 6HR 10/30 column (Pharmacia) eluted at a flow rate of 0.4 ml/min. with 10 mM sodium phosphate, pH 7.1, containing 150 mM NaCl. After ten hours, the size exclusion chromatography indicated that all of the protein (in solution as a dimer) has been converted to two possible forms of the N-terminally pegylated derivative: MPEG conjugated to one, or to both, N-termini of the NT-3 dimer.

The reaction mixture was then diluted a total of five times with 20 mM sodium phosphate, pH 7.1, and applied to a HiLoad 16/10 S Sepharose HP ion exchange column (Pharmacia) equilibrated with 20 mM sodium phosphate buffer, pH 7.1. The reaction mixture was loaded onto the column at a flow rate of 1 ml/min, and the unreacted MPEG aldehyde eluted with three column volumes of the same buffer. A linear gradient from 0% to 100% of 20 mM sodium phosphate, pH 7.1, containing 0.4M NaCl, was used to elute the two forms of the N-terminally pegylated NT-3 dimer. Fractions containing the MPEG-NT-3 derivatives were pooled, concentrated, and sterile filtered.

Additional MPEG-BDNF or MPEG-NT-3 conjugates can be obtained by modifying BDNF or NT-3 with MPEG aldehydes of different average molecular weight, for instance, ranging from 5 kDa to 50 kDa, can be prepared in a similar manner. The homogeneity of the resulting pegylated BDNF or NT-3 conjugates is determined by Sodium Dodecyl Sulfate Polyacrylamide Gel Electrophoresis (SDS-PAGE), using 10–20% or 4–20% precast gradient gels (Integrated Separation Systems). To characterize the effective size (hydrodynamic radius) of each MPEG-BDNF or MPEG-NT-3 species, a Superose 6 HR 10/30 (Pharmacia) gel filtration column is used. Proteins are detected by UV absorbance at 280 nm. The BIO-RAD gel filtration standards serve as globular protein molecular weight markers. The molecular weights of the conjugates are determined by sedimentation equilibrium analytical ultracentrifugation and by matrix-assisted laser desorption mass spectrometric analysis. The structure of each N-terminal MPEG-BDNF or MPEG-NT-3 conjugate is confirmed using standard methods of N-terminal protein sequencing and peptide mapping.

The in vitro biological activity of the MPEG-BDNF conjugates prepared in Examples 1–7 was determined by their effect on 3-(4,5-dimethylthiazol-2-yl)-5-(3-carboxymethoxyphenyl)-2-(4-sulfophenyl)2H-tetrazolium, inner salt uptake by PC12/pcDneo-trkB#18 cells. These results as well as principal reaction parameters used in the preparation of the conjugates are summarized in Table 1.

TABLE 1

Summary of MPEG-BDNF conjugate characteristics and major parameters of preparation reactions

|   | Conjugate | Reactive MPEG Type | MW, kDa | Reaction conditions pH | MPEG[a] BDNF | Conjugate characteristics MW,[b] kDa | MPEG[a] BDNF | Activ. in vitro |
|---|---|---|---|---|---|---|---|---|
|   | r-metHuBDNF | N/A | N/A | N/A | N/A | 27 | N/A | 100% |
| (1) | mono-MPEG-BDNF | Aldehyde | 6 | 4 | 4 | 111.8 | 2 | 101 |
| (2) | mono-MPEG-BDNF | Aldehyde | 20 | 5 | 4 | 483.8 | 2 | 73 |
| (3) | poly-MPEG-BDNF | Aldehyde | 6 | 8 | 8 | 110.1 | 2.4 | 82 |
| (4) | poly-MPEG-BDNF | Aldehyde | 6 | 8 | 12 | 257.2 | 4.6 | 25 |
| (5) | poly-MPEG-BDNF | NHS ester | 6 | 8 | 8 | 298.0 | 4.6 | 2 |
| (6) | poly-MPEG-BDNF | NHS ester | 6 | 8 | 2 | 113.2 | 2.3 | 28 |
| (7) | poly-MPEG-BDNF | NHS ester | 20 | 8 | 6 | 934.3 | 2.8 | 8 |

[a]- mole/mole of BDNF dimer
[b]- apparent MW determined by gel filtration
n/a - not applicable

EXAMPLE 9
Evaluation of In Vivo Biological Activity of Pegylated BDNF Conjugate on Motoneurons in Adult Rats BDNF has been shown previously to rescue developing motoneurons from naturally occurring and axotomy-induced cell death; Yan et al. *Nature* 360:753–755 (1992); Oppenheim et al., *Nature* 360:755–757 (1992); and Sendtner et al., *Nature* 360:757–759 (1992). It has also been demonstrated that axotomized adult motoneurons respond to exogenous BDNF, and more specifically, that BDNF applied by various modes of administration attenuates the axotomy-induced decrease of choline acetyltransferase (ChAT) immunoreactivity in the facial motoneurons of adult rats; Yan et al., *J. Neurosci.* 14(9):5281–5291 (1994). The decrease in ChAT activity is indicative of a loss in motoneuron function, since ChAT is a vital neurotransmitter produced by motoneurons. Thus, these studies indicate that BDNF is useful as a potential therapeutic agent for adult motoneuron diseases. In the present study, the biological activity of N-terminally pegylated and randomly pegylated species of BDNF (see Examples 1 and 3) on lesioned adult motoneurons in vivo is evaluated.

Methods

A. Animal surgery and treatment

Adult female Sprague-Dawley rats (total of 52 rats, n=4 for each group) were anesthetized with a cocktail (43 mg/ml of ketamine hydrochloride, 8.6 mg/ml of xylazine and 1.43 mg/ml of acepromazine) at a dose of 0.7 ml/kg body weight. The right facial nerve was transected near the stylo-mastoid foramen. Animals were treated subcutaneously once a day for seven days, starting on the day of surgery (day 0). The doses used were 0.1, 0.3, 1.0, and 5.0 mg per kg body weight of unpegylated BDNF, N-terminal monoMPEG(20 kDa)-BDNF conjugate, or random polyMPEG-BDNF conjugate, each in PBS. One group of rats were treated with PBS only as a control. Body weights of the animals were measured daily.

B. ChAT immunohistochemistry

Rats were sacrificed by an overdose of anesthesia and perfused transcardially with PBS, followed by 4% paraformaldehyde in 0.1M sodium phosphate buffer, pH 7.2. The brain stems were removed, cryoprotected with 30% sucrose in PBS, frozen onto a sliding microtome chuck, and 80 $\mu$m serial coronal sections were cut through the facial nucleus region. Sections were then processed for immunohistochemistry with mouse monoclonal antibody against ChAT (ascites, 1:500, Chemicon, Temecula, Calif.), followed by 2 $\mu$g/ml of secondary biotinylated horse anti-mouse antibody using the ABC method (Vector Laboratories, Burlingame, Calif.) described by Yan and Johnson in *J. Neurosci.* 8(9) :3481–3498 (1988).

C. Quantification of immunohistochemical sections

A Quantimet 520 image analyzer (Leica, Inc., Deerfield, Ill.) coupled to a Nikon Optiphot-FXA microscope was used to quantify the relative intensity of ChAT staining. A 510 nm narrow-band pass filter (Oriel Corp., Stratford, Conn.) was used with a Nikon-Plan Apochromatic 2× objective lens to produce high contrast images of the facial nucleus region in histology sections. The relative intensity of ChAT immunoreactivity was determined by obtaining the mean gray scale intensity for each outlined nucleus minus the background staining adjacent ChAT negative gray matter. For each animal, three or four sections containing the facial nucleus were used for the quantification. Since BDNF treatment did not affect the ChAT immunostaining of the non-lesioned facial nucleus, the data were expressed as the ratio of the relative optical density of lesioned over non-lesioned facial nuclei of same sections. The data were statistically analyzed by ANOVA followed by the Dunnett t test.

D. Results

Axotomy in adult rats causes a rapid and reproducible decrease of ChAT immunoreactivity in motoneurons; Lams et al., *Brain Res.* 475:401–406 (1988) and Armstrong et al., *J. Comp. Neurol.* 304:596–607 (1991). To evaluate the effects of unpegylated BDNF and pegylated BDNF on adult motoneurons, the facial nerve transection paradigm described above was used to study the influence of these polypeptides on the expression of ChAT in motoneurons.

Figure 1:
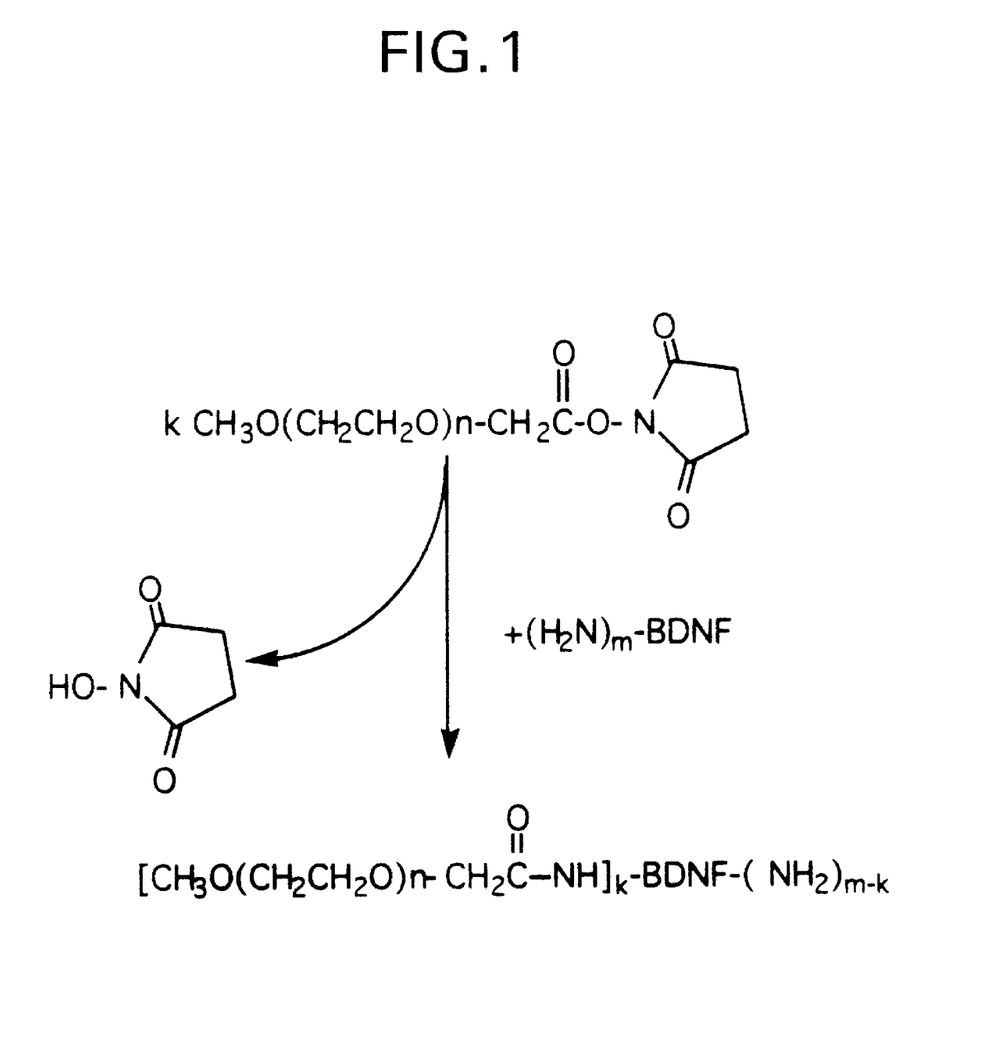
FIG. 1 shows an example of BDNF (or NT-3) acylation using N-hydroxysuccinimidyl (NHS) active esters of monomethoxypolyethylene glycol aldehydes to result in a polypegylated product. In the figure, k stands for the number of MPEG molecules reacted with a molecule of BDNF or NT-3, n stands for the degree of polymerization of MPEG used in the reaction (where n=2000 for MPEG having a molecular weight of 100 kDa and n=40 for MPEG having a molecular weight of 2 kDa), and m stands for the total number of primary amino groups per BDNF or NT-3 molecule.
Figure 2:
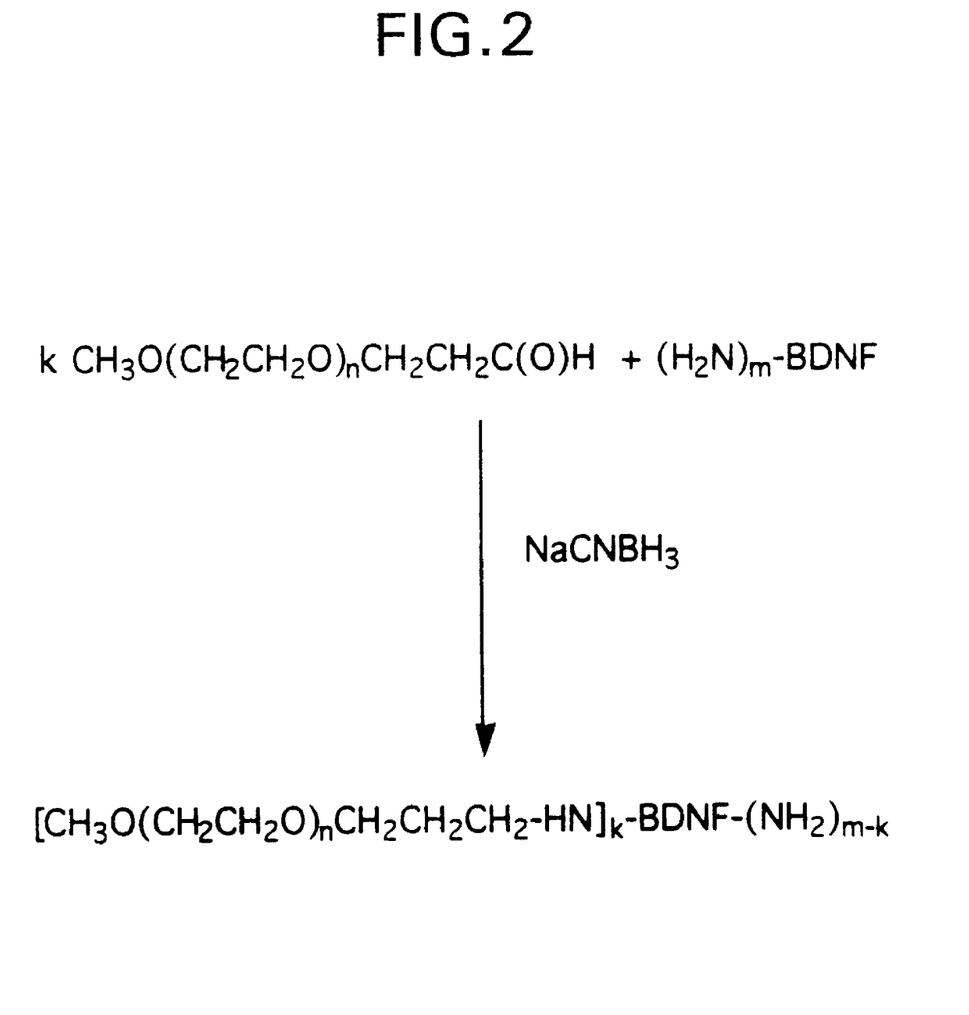
FIG. 2 shows an example of nonspecific reductive alkylation of BDNF (or NT-3) using monomethoxypolyethylene glycol-active aldehydes to result in a polypegylated product. In this figure, k, m and n are the same as defined above.
Figure 3:
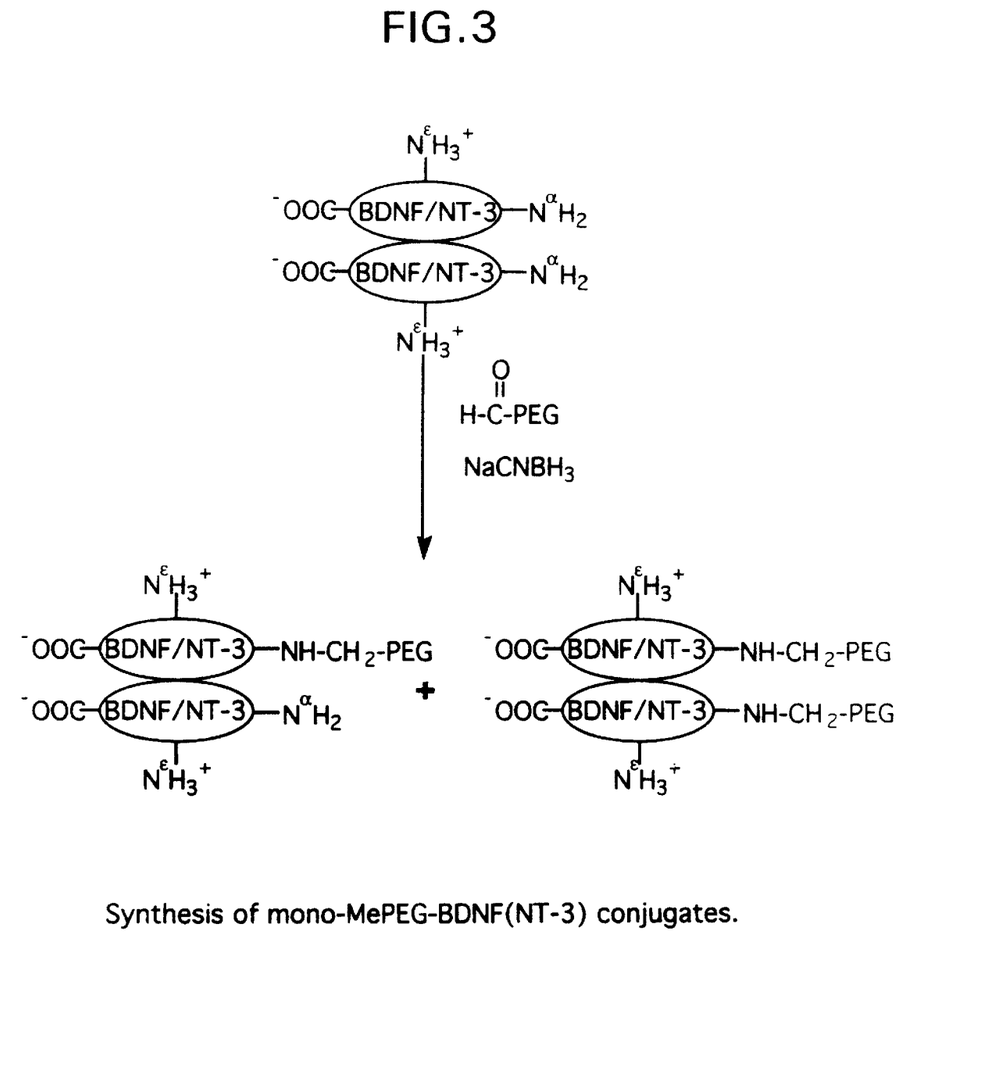
FIG. 3 shows an example of site-specific reductive alkylation of BDNF or NT-3 at the α-amino group of the N-terminal residue in the polypeptide, using monomethoxypolyethylene glycol active aldehydes to result in a substantially monopegylated product (at the N-terminus).
Figure 4A:
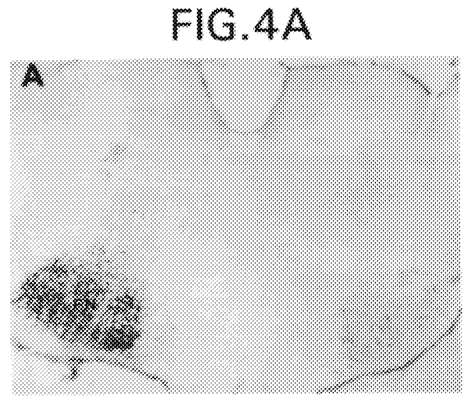
Figure 4B:
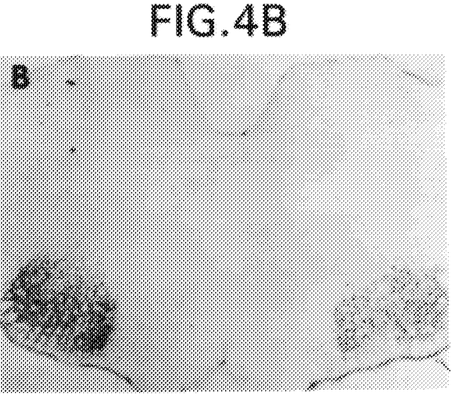
Figure 4C:
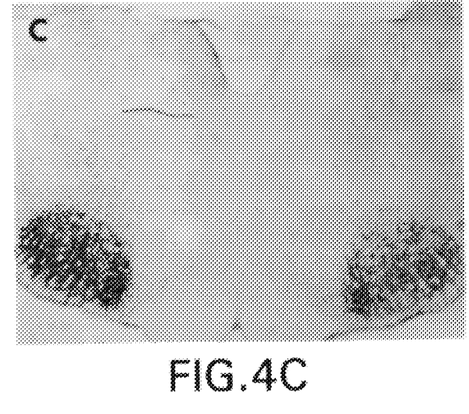
Figure 4D:
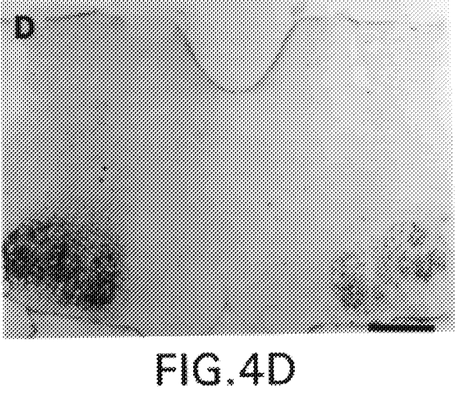
Figure 5:
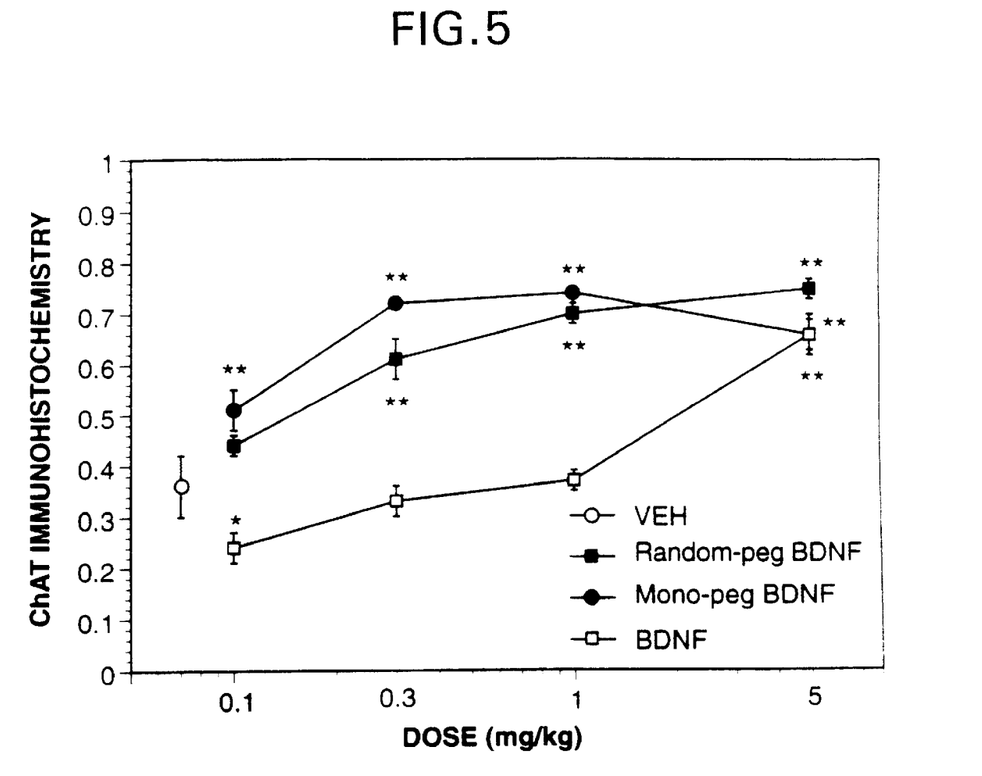
FIG. 5 shows a dose-response curve following treatment of test animals with unpegylated BDNF and pegylated BDNF in the same model of axotomized facial motoneurons as in FIG. 4. Animals received a daily subcutaneous injection (s.c.) of vehicle only (○), unpegylated BDNF (□), N-terminal pegylated BDNF (●) or randomly pegylated BDNF (■) at the doses indicated over a period of seven days. Values are stated as mean ± SEM (n=4). The data were analyzed by ANOVA followed by the Dunnett t test. *, $p<0.05$; **, p, 0.01, BDNF treatments versus vehicle.

Seven days after right facial nerve transection, ChAT immunoreactivity largely disappeared from the lesioned facial nucleus receiving PBS treatment (FIG. 4A the facial nucleus on the right hand side). Subcutaneous treatment with native BDNF (5 mg/kg, FIG. 4B) N-terminal monoMPEG-BDNF conjugate (0.3 mg/kg, FIG. 4C), and random polyMPEG-BDNF conjugate (0.3 mg/kg, FIG. 4D) significantly attenuated the lesion-induced decrease of ChAT immunoreactivity. To quantify this phenomenon, the average optical densities of both lesioned and non-lesioned facial nuclei of ChAT immunostained sections were measured. Native, N-terminal monoMPEG-BDNF conjugate and random polyMPEG-BDNF conjugate all reduced the lesion-induced decrease of CHAT immunoreactivity in a dose-dependent fashion (FIG. 5). Native BDNF at the 5 mg/kg dose showed a significant attenuation of the lesion-induced ChAT immunoreactivity decrease over the vehicle control ($p<0.01$). Treatment with either N-terminal monoMPEG-BDNF conjugate or random polyMPEG-BDNF conjugate resulted in a significant improvement over the vehicle control at each dose tested, and over native BDNF at the lower closes tested ($p<0.01$). By estimation, treatment with pegylated BDNF shifted the dose-response curve to the left about twenty-fold over native BDNF (FIG. 5), indicating an enhancement of the efficacy of pegylated BDNF on lesioned motoneurons.

EXAMPLE 10

Evaluation of In Vitro Biological Activity of N-terminal MonoMPEG-NT-3 Conjugate In Embryonic Chicken DRG Bioassay The comparative biological activities of unpegylated NT-3 and N-terminal monoMPEG(20 kDa)-NT-3 conjugate were measured using the embryonic chicken dorsal root ganglion (DRG) assay described by Lindsay et al. in *Dev. Biol.* 112:319–328 (1985). Briefly, five embryonic (E8) chick dorsal root ganglia per well were cultured as explants in a collagen matrix with 2 ml of F14 medium containing 5% normal horse serum. The effects of the neurotrophic factor (both unpegylated and pegylated) were assessed visually under a phase microscope and scored on a 0–5 scale (0=no neurite outgrowth, 5=maximum neurite outgrowth).

The results reported in Table 2, below, indicate that pegylated NT-3 suffered no loss of activity in comparison with unpegylated NT-3, a surprising result in view of experience with other pegylated proteins assayed in vitro which undergo substantial decreases in bioactivity.

TABLE 2

E8 Chicken DRG In Vitro Bioassay

| Factor | Sample Concen. (ng/ml) | Neurite Outgrowth |
| --- | --- | --- |
| NT-3 | 0.5 | 1, 2, 2, 3, 3 |
|  | 5 | 4, 4, 5, —, — |
|  | 10 | 0.5, 1, 1, 1, 2 |
|  | 50 | 0.5, 0.5, 0.5 1, 1 |
| Pegylated NT-3 | 5 | 4, 4, 4, 2, 2 |
|  | 50 | 3, 3, 2, 2, 1 |
|  | 500 | 0, 0.5, 0.5, 1, 2 |
|  | 1000 | 3, 3, 2, 1, 0.5 |

EXAMPLE 11

Further Evaluation of In Vivo Biological Activity of N-Terminal MonoPEG(20 kDa)-BDNF Conjugate in Adult Rats—Permeation Through Brain Tissue 1. Striatal single injection One microliter of unpegylated BDNF or N-terminal monoMPEG(20 kDa)-BDNF conjugate (1 mg/ml in phosphate buffer saline) was injected in vivo into the center of the right striatum of adult female rat brains (n=4) for 18–20 hrs. Twenty hours later, the animals were sacrificed by an overdose of anesthesia and perfused transcardially with PBS, followed by 4% paraformaldehyde in 0.1M sodium phosphate buffer, pH 7.2. The brains were removed, cryoprotected with 30% sucrose in PBS, frozen onto a sliding microtome chuck, and 60 μm serial coronal sections were cut. The sections were then processed for immunohistochemistry with 1 μm/ml of rabbit anti-BDNF antibody, followed by 2 μm/ml of secondary biotinylated goat anti-BDNF antibody using the ABC method referred to above. Very intense staining was seen in the injection site of the striatum with both the unpegylated and pegylated BDNF samples. Pegylated BDNF was seen to diffuse into a larger area of tissue than unpegylated BDNF, about 2.4-fold as seen in FIG. 6. There were a few neurons in the substantia nigra that were positively labeled (not shown).

2. Striatal seven day infusion

Figure 8A:
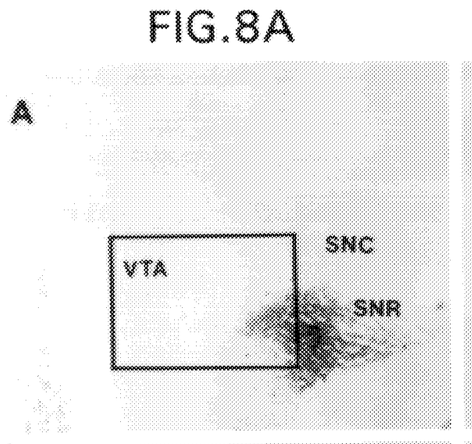
Figure 8B:
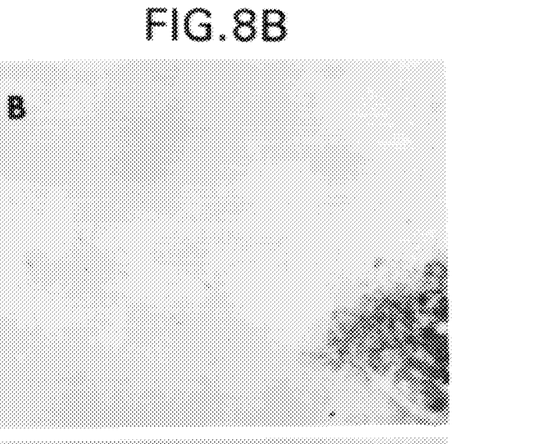
Figure 8C:
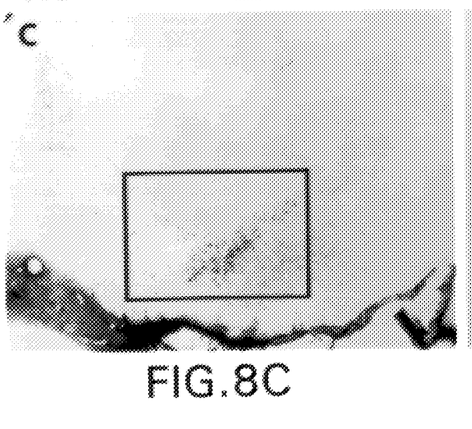
Figure 8D:
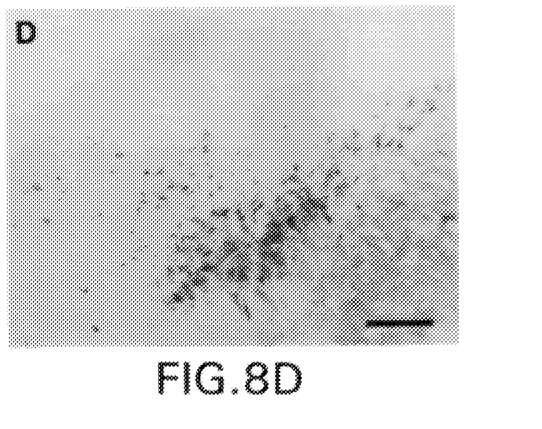

Adult female rats (n=4 received a daily infusion of 12 μg of either unpegylated BDNF or N-terminal monoMPEG(20 kDa)-BDNF conjugate in the striatum over a period of seven days. The penetration of both forms of BDNF was even better, in this study, than for the single injection protocol, above. Pegylated BDNF diffused into a much larger area than native BDNF, about 6.1-fold, as seen in FIG. 7. Many more neurons in the substantia nigra compacta ("SNC") and in the ventral tegmental area ("VTH") were positively labeled following infusion with pegylated BDNF (FIG. 8C, FIG. 8D) than with unpegylated BDNF (FIG. 8A, FIG. 8B). Under higher power magnification, BDNF-immunoreactivity was punctate and within the perikarya, which indicated that the BDNF had been retrogradely transported from the nerve terminal to the cell body. The positive staining seen in the medial ventral part of the substantia nigra reticulata ("SNR") was in the neuropil and was not associated with any cell bodies. This staining was due to non-specific diffusion instead of receptor-mediated retrograde transport; Ferguson et al., *J. Comp. Neurol.* 313:680–692 (1991).

These results are very significant. Typically, after parenchymal administration to the brain in animals, BDNF is found to diffuse through brain tissue very poorly. The present data show a dramatic improvement in the ability to achieve such diffusion when a pegylated BDNF is used, which is suggestive of potentially greater efficacy as a therapeutic at least for such forms of administration.

What is claimed:

1. A polyethylene glycol derivative of a polypeptide neurotrophic factor, wherein said polypeptide is connected to said polyethylene glycol, and said polypeptide is selected from the group consisting of brain-derived neurotrophic factor (BDNF) and neurotrophin-3 (NT-3).

2. A derivative according to claim 1, in which the polyethylene glycol is a mono-methoxy polyethylene glycol.

3. A derivative according to claim 1, in which the polyethylene glycol is attached to the polypeptide by an acyl or alkyl linkage.

4. A derivative according to claim 1, in which the polyethylene glycol has a molecular weight from about 2 to about 100 kDA.

5. A derivative according to claim 4, in which the polyethylene glycol has a molecular weight from about 5 kDa to about 50 kDa.

6. A method for attaching a polyethylene glycol molecule to a polypeptide selected from the group consisting of brain-derived neurotrophic factor (BDNF) and neurotrophin-3 (NT-3), wherein the polyethylene glycol has a single reactive aldehyde group, said method comprising:

(a) reacting the polypeptide with polyethylene glycol under reductive alkylation conditions, at a pH sufficiently acidic to allow the α-amino group at the amino terminus of said polypeptide to be reactive, whereby the polyethylene glycol becomes attached at said α-amino group;

(b) recovering the polypeptide monopegylated at said N-terminal α-amino group in substantially homogeneous form.

7. A method according to claim 6, wherein the reductive alkylation conditions involve the use of sodium cyanoborohydride as a reducing agent.

8. A method according to claim 6, wherein the polyethylene glycol molecule has a molecular weight from about about 2 kDa to about 100 kDa.

9. A method according to claim 6 in which the polypeptide is BDNF.

10. A method according to claim 6 in which the polypeptide is NT-3.

11. A method according to claim 6; wherein the pH is between about 3 and about 9.

12. A method according to claim 11 in which the pH is between 3 and 6.

13. A substantially homogeneous preparation of brain-derived neurotrophic factor (BDNF) monopegylated at the α-amino group at the N-terminus.

14. A pharmaceutical composition comprising the monopegylated BDNF of claim 13 and a pharmaceutically acceptable carrier.

15. A substantially homogeneous preparation of neurotrophin-3 (NT-3) monopegylated at the α-amino group at the N-terminus.

16. A pharmaceutical composition comprising the monopegylated NT-3 of claim 15 and a pharmaceutically acceptable carrier.

* * * * *

UNITED STATES PATENT AND TRADEMARK OFFICE
CERTIFICATE OF CORRECTION

PATENT NO. : 5,770,577
DATED : June 23, 1998
INVENTOR(S) : OLAF KINSTLER and QIAO YAN It is certified that error appears in the above-identified patent and that said Letters Patent is hereby corrected as shown below:

Column 10, line 64, change "kdDa" to --kDa--.

Column 11, line 2, change "kdDa" to --kDa--.

Sequence List, Seq. ID No. 1, Residue 72, change "Asx" to --Asp--.

Sequence List, Seq. ID No. 2, Residue 88, change "Asx" to --Val--.

Sequence List, Seq. ID No. 2, Residue 111, change "Asx" to --Val--.

Signed and Sealed this

Fifteenth Day of December, 1998

Attest:

Attesting Officer

BRUCE LEHMAN

Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:1:

```
His Ser Asp Pro Ala Arg Arg Gly Glu Leu Ser Val Cys Asp Ser Ile
 1               5                  10                  15
Ser Glu Trp Val Thr Ala Ala Asp Lys Lys Thr Ala Val Asp Met Ser
            20                  25                  30
Gly Gly Thr Val Thr Val Leu Glu Lys Val Pro Glu Ser Lys Gly Gln
        35                  40                  45
Leu Lys Gln Tyr Phe Tyr Glu Thr Lys Cys Asn Pro Met Gly Tyr Thr
    50                  55                  60
Lys Glu Gly Cys Arg Gly Ile Asx Lys Arg His Trp Asn Ser Gln Cys
65                  70                  75                  80
Arg Thr Thr Gln Ser Tyr Val Arg Ala Leu Thr Met Asp Ser Lys Lys
                85                  90                  95
Arg Ile Gly Trp Arg Phe Ile Arg Ile Asp Thr Ser Cys Val Cys Thr
            100                 105                 110
Leu Thr Ile Lys Arg Gly Arg
        115
```

( 2 ) INFORMATION FOR SEQ ID NO:2:

( i ) SEQUENCE CHARACTERISTICS:
        ( A ) LENGTH: 120 amino acids
        ( B ) TYPE: amino acid (C) STRANDEDNESS: single
(D) TOPOLOGY: linear (ii) MOLECULE TYPE: protein (xi) SEQUENCE DESCRIPTION: SEQ ID NO:2:

Met His Ser Asp Pro Ala Arg Arg Gly Glu Leu Ser Val Cys Asp Ser
1               5                   10                  15

Ile Ser Glu Trp Val Thr Ala Ala Asp Lys Lys Thr Ala Val Asp Met
            20                  25                  30

Ser Gly Gly Thr Val Thr Val Leu Glu Lys Val Pro Val Ser Lys Gly
        35                  40                  45

Gln Leu Lys Gln Tyr Phe Tyr Glu Thr Lys Cys Asn Pro Met Gly Tyr
    50                  55                  60

Thr Lys Glu Gly Cys Arg Gly Ile Asp Lys Arg His Trp Asn Ser Gln
65                      70                  75                  80

Cys Arg Thr Thr Gln Ser Tyr Asx Arg Ala Leu Thr Met Asp Ser Lys
                85                  90                  95

Lys Arg Ile Gly Trp Arg Phe Ile Arg Ile Asp Thr Ser Cys Asx Cys
            100                 105                 110

Thr Leu Thr Ile Lys Arg Gly Arg
        115                 120

(2) INFORMATION FOR SEQ ID NO:3:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Tyr Ala Glu His Lys Ser His Arg Gly Glu Tyr Ser Val Cys Asp Ser
1               5                   10                  15

Glu Ser Leu Trp Val Thr Asp Lys Ser Ser Ala Ile Asp Ile Arg Gly
            20                  25                  30

His Gln Val Thr Val Leu Gly Glu Ile Lys Thr Gly Asn Ser Pro Val
        35                  40                  45

Lys Gln Tyr Phe Tyr Glu Thr Arg Cys Lys Glu Ala Arg Pro Val Lys
    50                  55                  60

Asn Gly Cys Arg Gly Ile Asp Asp Lys His Trp Asn Ser Gln Cys Lys
65                      70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
            100                 105                 110

Ser Arg Lys Ile Gly Arg Thr
        115

(2) INFORMATION FOR SEQ ID NO:4:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Met 1 | Tyr | Ala | Glu | His 5 | Lys | Ser | His | Arg | Gly 10 | Glu | Tyr | Ser | Val | Cys 15 | Asp |
| Ser | Glu | Ser | Leu 20 | Trp | Val | Thr | Asp | Lys 25 | Ser | Ser | Ala | Ile | Asp 30 | Ile | Arg |
| Gly | His | Gln 35 | Val | Thr | Val | Leu | Gly 40 | Glu | Ile | Lys | Thr | Gly 45 | Asn | Ser | Pro |
| Val | Lys 50 | Gln | Tyr | Phe | Tyr | Glu 55 | Thr | Arg | Cys | Lys | Glu 60 | Ala | Arg | Pro | Val |
| Lys 65 | Asn | Gly | Cys | Arg | Gly 70 | Ile | Asp | Asp | Lys | His 75 | Trp | Asn | Ser | Gln | Cys 80 |
| Lys | Thr | Ser | Gln | Thr 85 | Tyr | Val | Arg | Ala | Leu 90 | Thr | Ser | Glu | Asn | Asn 95 | Lys |
| Leu | Val | Gly | Trp 100 | Arg | Trp | Ile | Arg | Ile 105 | Asp | Thr | Ser | Cys | Val 110 | Cys | Ala |
| Leu | Ser | Arg 115 | Lys | Ile | Gly | Arg | Thr 120 | | | | | | | | |